United States Patent [19]
Farrell

[11] Patent Number: 5,624,257
[45] Date of Patent: *Apr. 29, 1997

[54] ORAL APPLIANCE

[76] Inventor: Christopher J. Farrell, P.O. Box 7699, Gold Coast Mail Centre, Queensland 4217, Australia

[*] Notice: The term of this patent shall not extend beyond the expiration date of Pat. No. 5,259,762.

[21] Appl. No.: 232,012
[22] PCT Filed: Nov. 2, 1992
[86] PCT No.: PCT/AU92/00592
§ 371 Date: May 2, 1994
§ 102(e) Date: May 2, 1994
[87] PCT Pub. No.: WO93/08761
PCT Pub. Date: May 13, 1993

Related U.S. Application Data

[63] Continuation-in-part of Ser. No. 838,198, Mar. 6, 1992, Pat. No. 5,259,762.

[30] Foreign Application Priority Data

Oct. 31, 1991 [AU] Australia ............... PK9220

[51] Int. Cl.⁶ .................................. A61C 7/00
[52] U.S. Cl. ............................. 433/6; 128/861
[58] Field of Search .................. 433/6, 37, 41, 433/215; 128/859, 861, 848, 860

[56] References Cited

U.S. PATENT DOCUMENTS

| | | | |
|---|---|---|---|
| 347,976 | 8/1886 | Starr | 433/41 |
| 1,652,910 | 12/1927 | Psayla | 433/41 |
| 2,630,117 | 3/1953 | Coleman | 128/861 |
| 3,247,844 | 4/1966 | Berghash | 128/136 |
| 3,411,501 | 11/1968 | Greenberg | 128/136 |
| 3,898,736 | 8/1975 | Bergersen | 433/6 |
| 4,227,822 | 10/1980 | Tureaud et al. | 433/41 |
| 4,568,280 | 2/1986 | Ahlin | 433/6 |
| 4,784,605 | 11/1988 | Bergersen | 433/6 |
| 4,799,500 | 1/1989 | Newbury | 128/859 |
| 5,092,346 | 3/1992 | Hays et al. | 128/848 |
| 5,163,840 | 11/1992 | Bourke | 433/6 |
| 5,259,762 | 11/1993 | Farrell | 433/215 |
| 5,462,066 | 10/1995 | Snyder | 128/848 |
| 5,467,783 | 11/1995 | Meade | 128/848 |

FOREIGN PATENT DOCUMENTS

| | | | |
|---|---|---|---|
| 885595 | 6/1953 | Germany | 433/41 |
| 8002368 | 11/1980 | WIPO | 433/215 |

Primary Examiner—Cary E. O'Connor
Attorney, Agent, or Firm—Shoemaker and Mattare Ltd.

[57] ABSTRACT

An appliance for repositioning the temporomandibular joint has a base portion and inner and other flanges which form upper and lower U-shaped channels for receiving the teeth of the upper and lower jaws. The inner flange has a central tab and a pair of slots on opposite sides of the tab to allow for lateral adjustment of the appliance. In an alternative embodiment, the appliance has ribs on the outer flange, to engage the teeth of the user.

20 Claims, 11 Drawing Sheets

ORAL APPLIANCE

This application is a continuation-in-part of U.S. application Ser. No. 07/838,198, filed Mar. 6, 1992, now U.S. Pat. No. 5,259,762.

FIELD OF THE INVENTION

This invention relates to an oral appliance and in particular to an orthopaedic or orthodontic repositioning appliance.

DESCRIPTION OF THE PRIOR ART

Headache and jaw problems are often associated with incorrect harmony of the muscles and nerves of the jaw, skull and neck mechanism, an area called the Cranio-Mandibular System. A part of this system is the temporomandibular joint (TMJ) which comprises the joint which connects the lower jaw or mandible to the skull with temporal muscles in the region of the joint suspending the mandible from the skull. These muscles are used inter alia for speaking, swallowing eating and breathing and permit the mandible to be open and closed and moved forwardly and to the rear.

In a perfect bite with correct dental occlusion, the teeth of the upper and lower jaws come together. Misalignment of the upper and lower jaws however is a common occurrence caused by lack of development of the lower jaw resulting in a deep bite curve between the teeth of the upper and lower jaws. Misalignment of the joint caused by structural imbalances or other reasons can also cause a number of problems including headache, neck tension, curvature of the spine, muscular weakness and poor coordination. Furthermore, it has been found that a person loses strength when the joint is out of alignment. When the joint is under stress due to imbalance, the body uses up muscular strength causing fatigue and pain. In the case of athletes, misalignment of the joint results in decreased performance. A further underlying factor in the dysfunction in the muscular complex of the Cranio Mandibular System is the incorrect function or positioning of the tongue.

It has been found that by aligning the TMJ, dramatic improvements in athletic capabilities occur, in particular strength. Custom fitted plastic bite plates known as mandibular orthopedic repositioning appliances (MORA) have been proposed to relax the temporal muscles so as to permit the muscles to rest from their constant strain and thus relieve headaches and neck tension and in the case of athletes, to improve athletic performances. Such appliances however are required to be custom fitted to the user by taking impressions from the jaw and subsequently moulding the bite place. Such appliances have proved to be relatively expensive and of limited applicability.

Other oral devices are also used for a number of other purposes. For example, mouthguards are commonly used in sporting applications to protect the teeth of a user against damage. Such mouthguards range from inexpensive (and relatively inefficient) devices which the user shapes his- or herself to the form of the jaws or teeth to the more expensive devices fitted by dentists or orthodontists. In each case, the known mouthguards are intended only for protection purposes and have, and are intended to have, no other function.

There is also known in the art an oral appliance which is used primarily for teeth cleaning purposes. Such an appliance is in the general form of a mouthguard but is formed of relatively flexible material and is provided with a plurality of projections which serve when the appliance is worn to remove food particles from between the teeth. Such an appliance is only used on a short term basis for cleaning and again has no other purpose.

Another form of mouth appliance which is well known is the dummy which may be of many different forms and which is primarily used to pacify babies and young children. Generally however dummies can have a detrimental affect on teeth formation and positioning.

A number of dental appliances have been available in the past to correct tooth alignment. Such devices vary from orthodontic brackets, specially made removable appliances, both functional and non-functional, and orthodontic repositioners. Examples of the type of devices which have been proposed are shown in U.S. Pat. Nos. 3,178,820, 3,478,742, 3,510,946, 3,848,335 and 4,919,612. Generally such devices are specially manufactured in a laboratory with specific indentations for the teeth to be positioned or clipped onto and are manufactured in a multitude of sizes to match varying size mouths. Additionally some devices are required to be fitted directly onto the teeth.

SUMMARY OF THE INVENTION

The present invention aims to provide an oral appliance which in one aspect has the effect of repositioning the temporomandibular joint and which may be simply and easily used by a user. The present invention aims also to provide an oral appliance which is relatively inexpensive and which may be manufactured in one size to fit the majority of adults irrespective of race and requiring no moulding or trimming.

In one form, the present invention is embodied in an oral appliance which may be used for the relief of the symptoms of muscle tension headaches. In yet a further form, the present invention is embodied in an oral appliance suitable for improving performance in particular sports. The present invention in a yet a further form is embodied in an oral appliance suitable for use as a children's dummy or pacifier.

The present invention in another aspect aims to provide an oral appliance for use in orthodontic and orthopedic correction particularly in the facial area of children which overcomes or at least alleviates the disadvantages of the known devices. Other objects and advantages of the invention will become apparent from the following description.

With the above and other objects in view, the present invention provides in a first aspect an oral appliance adapted for repositioning the temporomandibular joint, said appliance including a base portion shaped so as to be locatable between the teeth of the upper and lower jaws of a user, and outer and inner flange portions along the leading and trailing edges of said base portion and extending to opposite sides thereof so as to form upper and lower channels for accepting the teeth of the upper and lower jaws, said inner flange portion defining a concave recess for receiving the tongue of the user, said base portion having a cross sectional form adapted to substantially occupy the space between said teeth of said upper and lower jaws so as to provide a support for the jaws of the user, and said inner flange portion being provided on its upper side with a slot or cutaway region arranged at or adjacent the midline of said appliance whereby said appliance may adjust laterally to fit the jaws of the user.

The present invention also provides a method for relieving the symptoms of muscle tension headaches, said method including the steps of placing an appliance of the above type in the mouth of a headache sufferer, closing the teeth on said appliance and maintaining said appliance in the mouth for an extended period of time suitably in the region of one hour.

Preferably, the base portion is of generally U-shaped or parabolic plan form and tapers in thickness along the channels on each side of the appliance from regions forwardly of but adjacent to the trailing ends of said appliance towards the leading end thereof. Preferably, also, said base portion tapers in thickness from said regions to the trailing ends of said appliance. The base portion is thus designed to substantially occupy the space between the upper and lower jaws resulting from a deep bite curve to put more pressure on the rear molars thereby relaxing and exercising the joints and muscles. Most preferably, the variation in thickness in the base portion is achieved by forming the base portion on opposite sides of the appliance asymmetrically with the top side of the base portion being generally planar or flat. Suitably, the base portion is formed as an asymmetric aerofoil shape with the asymmetric or curved surface thereof being disposed on the operative lower side of the appliance and the maximum depth of the aerofoil being located at a said region on opposite sides of said appliance.

Preferably, the inner flange portion is provided with a pair of spaced slots or cut-away portions disposed symmetrically on opposite sides of the midline of the appliance to define therebetween a tab, said tab preferably having an increased thickness relative to the remainder of the flange portion to provide an abutment for the tongue of the user whereby the tongue is encouraged or reminded to adopt a normal position. Preferably also, the junction between the base portion and the inner flange portion on opposite sides of the appliance is thickened or enlarged so that the appliance is adapted to the shape of the teeth of the user.

When the appliance of the invention is used for sporting or other purposes, it is suitably centrally apertured through the outer flange portions and/or the base portion so as to facilitate breathing by the user. Alternatively, a series of apertures may be formed through the outer flange portion for this purpose.

When the appliance of the invention is applied for usage as a dummy or pacifier, it is suitably provided with a handle which in use is arranged externally of the mouth of a user.

When the base portion is formed as above, the lower jaw of the user is moved downwardly and forwardly so that the jaws of the user are fully supported and so that muscles about the jaw are in a relaxer or substantially relaxed state.

The appliance of the invention is suitably formed of a flexible material such as silicone or PVC material which may readily deflect to fit the mouth of the user.

In a second aspect, the present invention provides an oral appliance for orthodontic or orthopedic correction, said appliance including a base portion shaped so as to be locatable between the teeth of the upper and lower jaws of a user, and outer and inner flange portions along the leading and trailing edges of said base portion and extending to opposite sides thereof so as to form upper and lower channels for accepting the teeth of the upper and lower jaws and wherein said base portion has a cross sectional form adapted to substantially occupy space between said teeth of said upper and lower jaws so as to provide a support for the jaws of the user, said outer flange portion being provided with rib means on its inner surface on opposite sides of and spaced from said base portion, said rib means extending generally parallel to said base portion and adapted to in use engage the teeth of the user.

This appliance may also have on its inner flange a cut-away region or slot to allow for lateral adjustement of the appliance. Preferably also an integral rib or enlargement is formed at the junction of the inner flange portion and base portion preferably on both sides thereof so that the teeth of the user are positioned in use between such ribs and the rib means on the inner surface of the outer flange portion. The outer flange portion may also be provided at least in its lower half with a series of protrusions for engaging the mentalis muscle.

BRIEF DESCRIPTION OF THE DRAWINGS

In order that the invention may be more readily understood and put into practical effect, reference will now be made to the accompanying drawings which illustrate a preferred embodiment of the invention and wherein.

DETAILED DESCRIPTION OF THE INVENTION

Figure 1:
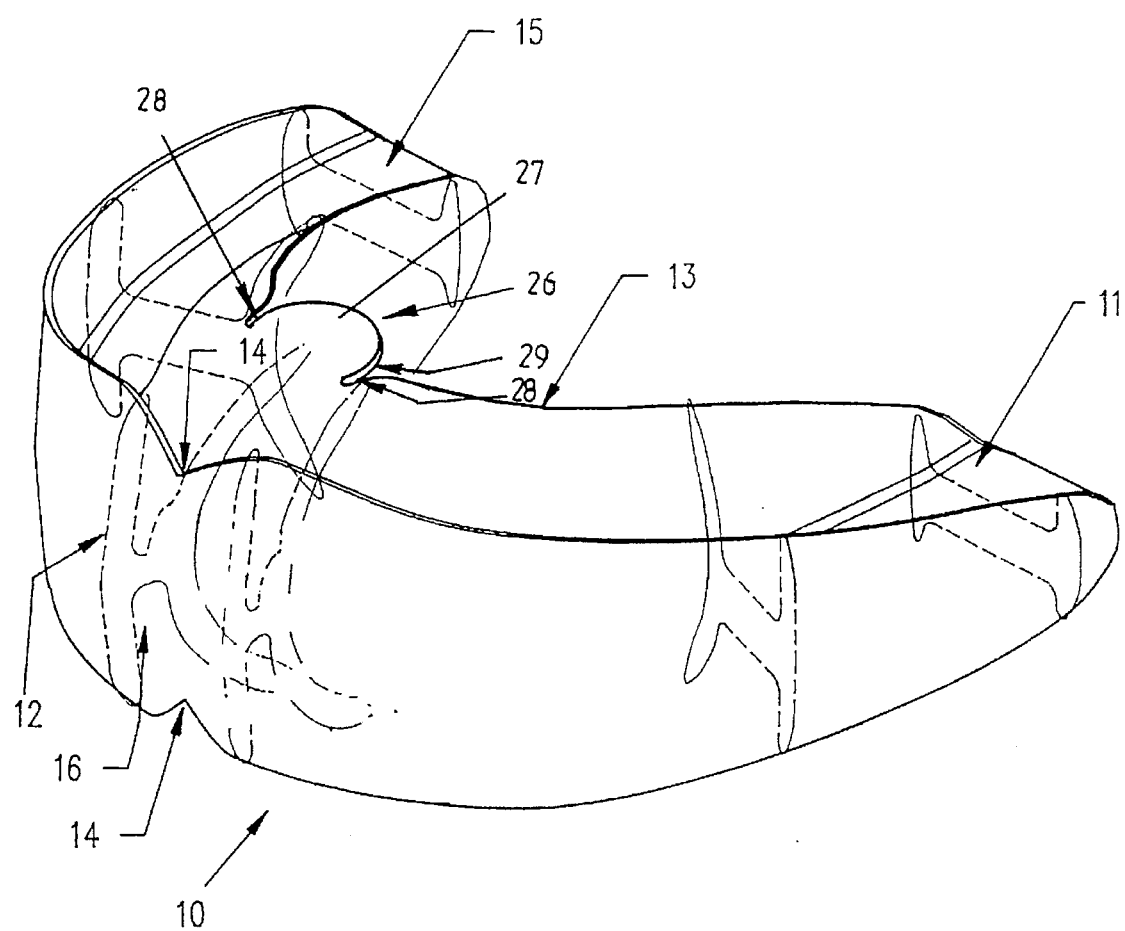
FIG. 1 is a perspective view of one form of oral appliance according to the present invention.

Referring to the drawings and firstly to FIGS. 1 to 4, there is illustrated a first form of oral appliance 10 according to the present invention. The appliance 10 includes a base portion 11 which is of a somewhat parabolic or U-shaped plan form so as to follow substantially the shape of the jaws and teeth pattern of a person. The base portion 11 is provided along its leading edge with an outer or labial flange portion 12 and along its trailing edge with an inner or lingual flange portion 13. The flange portions 12 and 13 define with the base portion 11 upper and lower channels 15 and 16 for receipt of the teeth of the upper and lower jaws. The outer and inner flange portions 12 and 13 are shaped to the labial and lingual aspects of the upper and lower jaws whilst at the central leading portion of the appliance 10, upper and lower locating cut-outs or notches 14 are provided in the flange portion 12.

Figure 2:
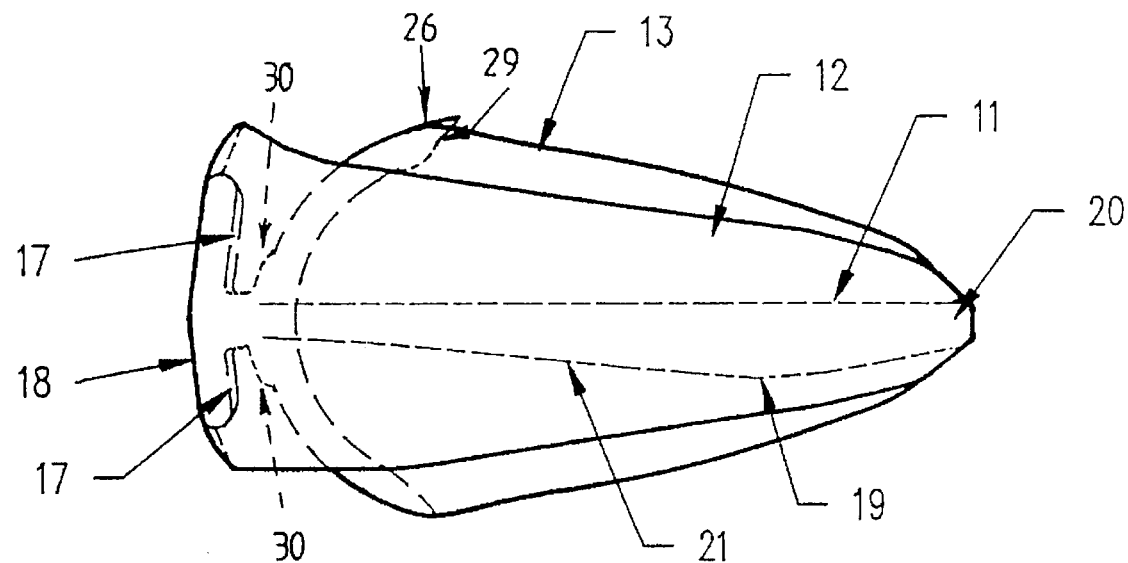
FIG. 2 illustrates in side view the appliance of FIG. 1.
Figures 12, 13:
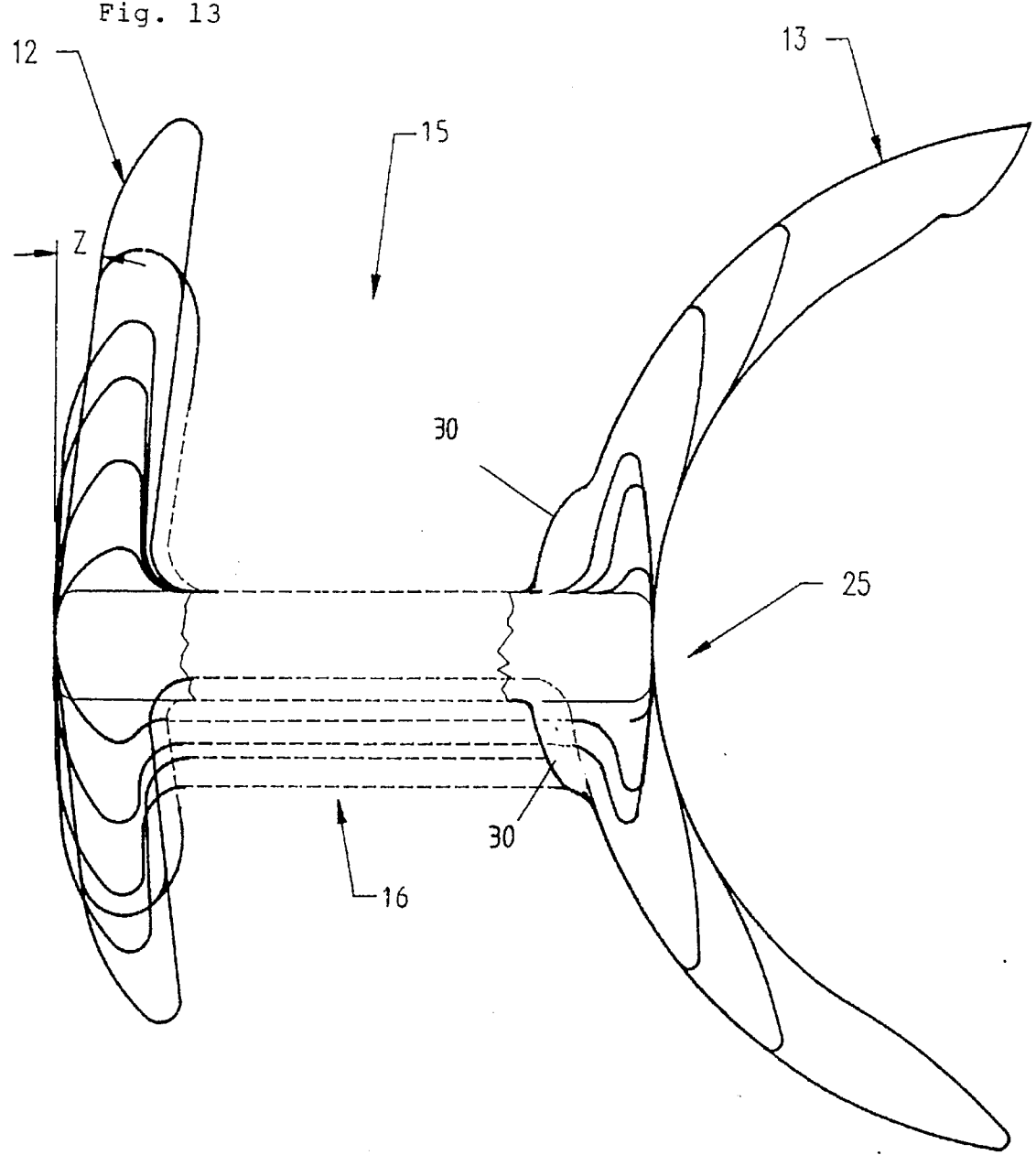
FIG. 12 is a sectional view along line H—H of FIG. 5.
FIG. 13 illustrates the sections of FIGS. 5 to 11 overlaid.

The appliance 10 as shown in FIG. 2 may also include upper and lower ribs 17 which as shown more clearly in FIG. 12 may have a triangular cross section, the ribs 17 being arranged centrally at the leading end of the appliance and extending into the channels 15 and 16. The ribs 17 are provided for positioning the appliance centrally within the mouth of the user for location between the front two teeth of the upper and lower jaw.

Figure 3:
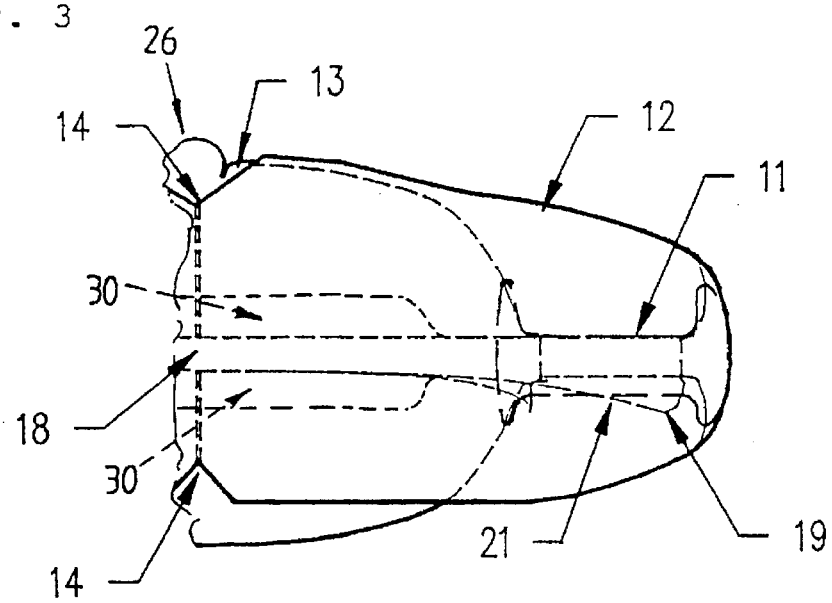
FIG. 3 is a half front elevational view of the appliance of FIG. 1.
Figure 4:
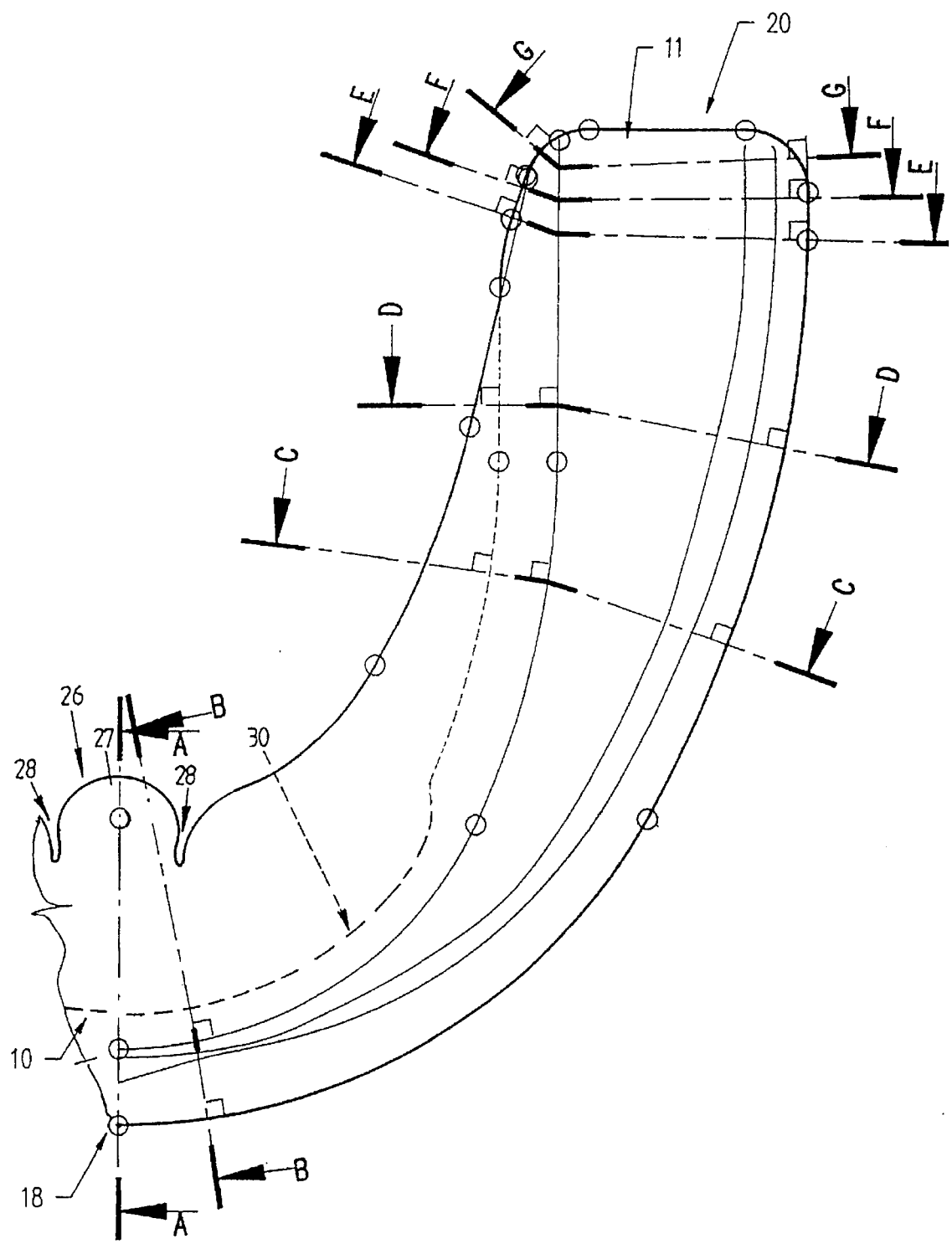
FIG. 4 is a half plan view of the appliance of FIG. 1.
Figure 5:
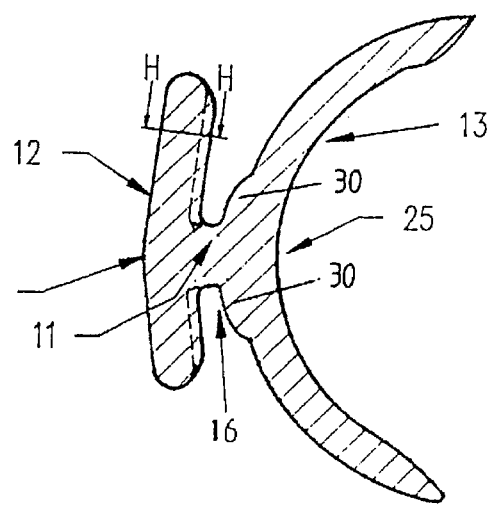
FIGS. 5 to 11 are sectional views of the appliance along lines A—A, B—B, C—C, D—D, E—E, F—F, and G—G respectively of FIG. 4.
Figure 6:
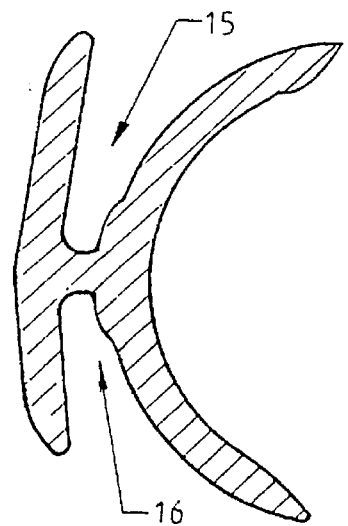
Figure 7:
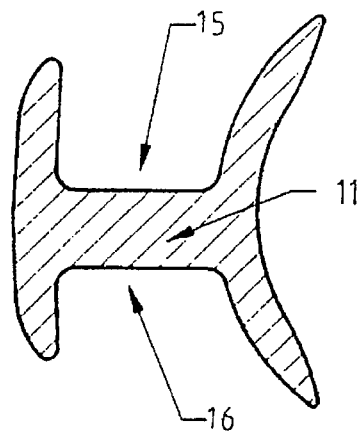

The base portion 11 of the appliance 10 most preferably has a thickness which tapers towards the central leading end 18 of the appliance in the manner shown in FIGS. 2 and 3 from a maximum at regions 19 arranged towards but spaced from the trailing ends 20 of the appliance and then tapers to the trailing and leading ends of the appliance from those regions 19 so as to form a shape of a substantially asymmetric aerofoil with the asymmetric or curved surface 21 of the aerofoil being located on the lower side of the appliance 10. Suitably, the base portion 11 has a thickness of approximately 1 mm to 3 mm, adjacent the leading end 18 of the appliance which increases to a maximum thickness of approximately 3.5 to 5 mm, at the regions 19 which are adjacent the first molar and then reduces to a thickness of approximately 2 to 3 mm, at the trailing ends 20.

As shown more clearly in FIGS. 5 to 11, the inner and outer flanges 12 and 13 define the upper and lower channels 15 and 16 for receipt of the teeth of the upper and lower jaws with the channels 15 and 16 for this purpose increasing in width from the central leading end 18 of the appliance 10 to the trailing ends 20 thereof. As is apparent also the flanges 12 and 13 taper in height from the leading end 18 of the appliance 10 to the trailing ends 20 thereof.

Figure 8:
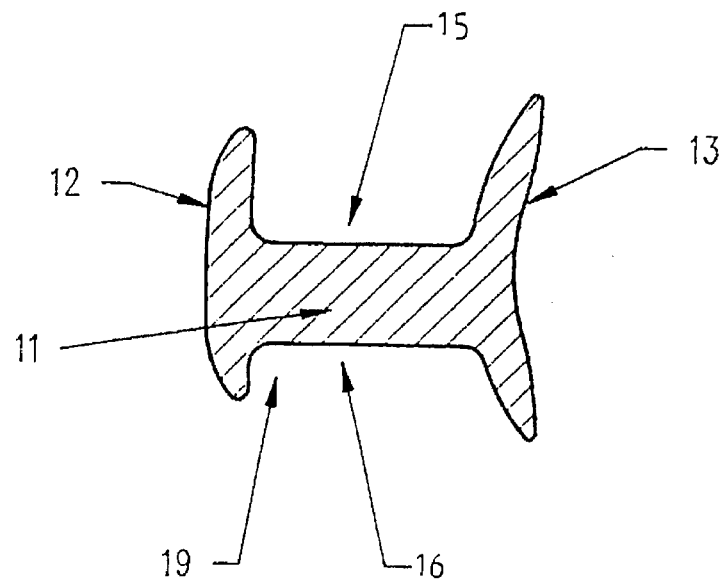
Figure 11:
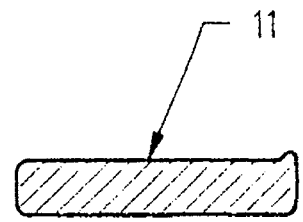

The base portion 11 is generally planar or flat on its top side whilst as described above, the base portion 11 increases in thickness from the leading end 18 of the appliance to a maximum at the region shown at FIG. 8 from where it reduces in thickness to the section shown in FIG. 11.

As is more apparent in FIG. 13, the front flange 12 is inclined to the vertical away from the leading end 18 of the appliance 10 on opposite sides of the base portion 11. The angle of inclination of the flange 12 (marked Z in FIG. 13) on the upper side of the base portion 11 decreases from a maximum at a position at the leading end 18 of the appliance (see FIG. 5) to zero towards the trailing end 20 shown at FIG. 9. Suitably the maximum angle of inclination is in the region of 7 degrees. Furthermore, the upper and lower portions of the flange 13 merge into each other at the base portion 11 through a radiused section 24 and the radius of the radiused section decreases to that shown in FIG. 9 after which it increases until the curve flattens to a substantially perpendicular line as shown in FIG. 11.

The trailing flange 13 is of generally parabolic cross section so as to define a rearwardly directed recess 25 for encompassing the tongue of the user in its correct anatomical position in the mouth and so as to improve retention of the device in the oral cavity.

Figure 9:
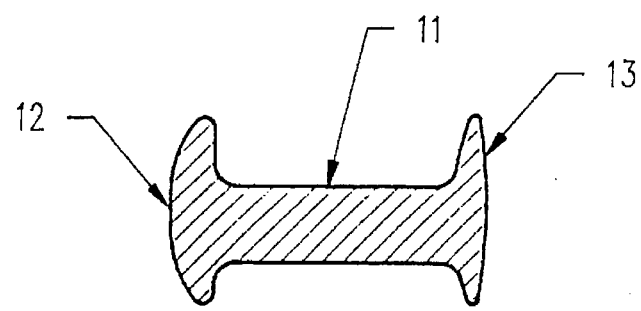
Figure 10:
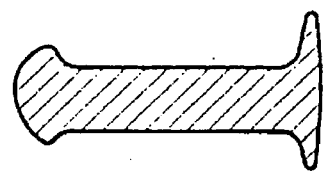

The leading face of the flange 13 preferably stays on the same radius from the leading to the trailing ends of the appliance although the width of the flange 13 reduces as is apparent in FIGS. 9 and 10 approaching the trailing ends of the appliance 10. At the trailing side of the flange 13, the surface of the flange 13 is disposed along the same radius forming a concavity however the width of the flange 13 on either side of the base portion 11 reduces so that the concave curve merges into a convex curve which flattens as shown in FIG. 11 to a perpendicular line at the trailing ends of the apparatus.

The inner flange portion 13 as shown more clearly in FIGS. 1 and 2 includes on its upper side and at its training edge a central tongue restrainer 26 which is in the form of a tab 27 formed between a pair of slots 28 in the flange 13, the slots 28 being arranged symmetrically relative to the midline of the appliance 10. The slots 28 have an important function in so far as they allow inward and outward movement of the opposite arms of the appliance 10. This allows various arch sizes of the population to be accommodated so that the appliance 10 will adapt to both narrow and broad arches without fundamental change in shape.

The tab 27 additionally is formed on its underside with a bulge or protrusion 29 which projects below the adjacent surfaces of the flange 13 so as to present an abutment to the tongue of the user. Thus when swallowing, the tongue will tend to come into engagement with the bulge or protrusion 29 and thereby be encouraged to adopt a normal functional position.

The flange portion 13 is also provided on its inner surface adjacent its junction with the base portion 11 with an integrally formed rib-like enlargement 30 (as shown in FIGS. 2 to 6) which adapts the appliance 10 to the general shape of the teeth of the user. The rib-like enlargements 30 which are provided both on the upper and lower sides of the appliance 10 extend symmetrically on opposite sides of the appliance and part way along the respective channels 15 and 16.

Figure 16:
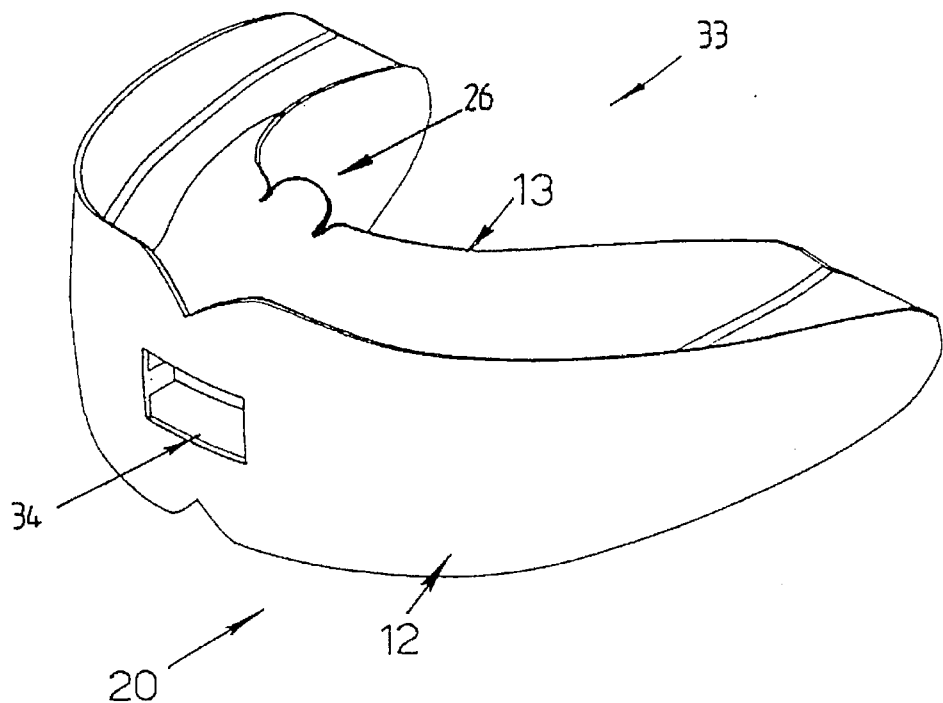
FIGS. 16 and 17 illustrate the application of the appliance of the invention to a sports appliance and dummy respectively.

FIG. 16 illustrates a further embodiment of appliance 33 suited to sports appliance applications. This embodiment is similar to the above described embodiment and accordingly like parts have been given like numerals. In this case however, the base portion 11 has an increased thickness whilst retaining the substantially aerofoil shape with a suitable maximum thickness being up to 4 to 6 mm. greater than the dimensions stated above for normal usage. Furthermore, in this embodiment, the central region of the appliance is apertured through the flange 12 and base portion 11 so as to define a large air breathing hole 34 necessary for sports applications.

Figure 17:
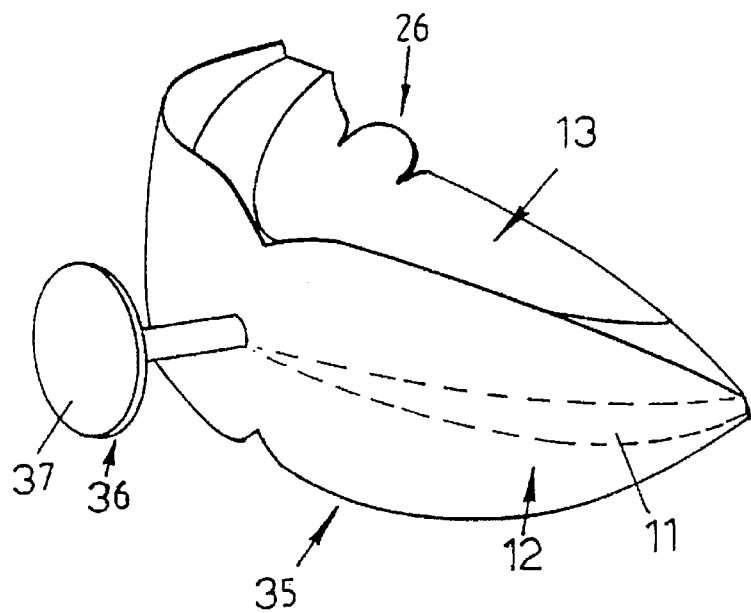
Figure 18:
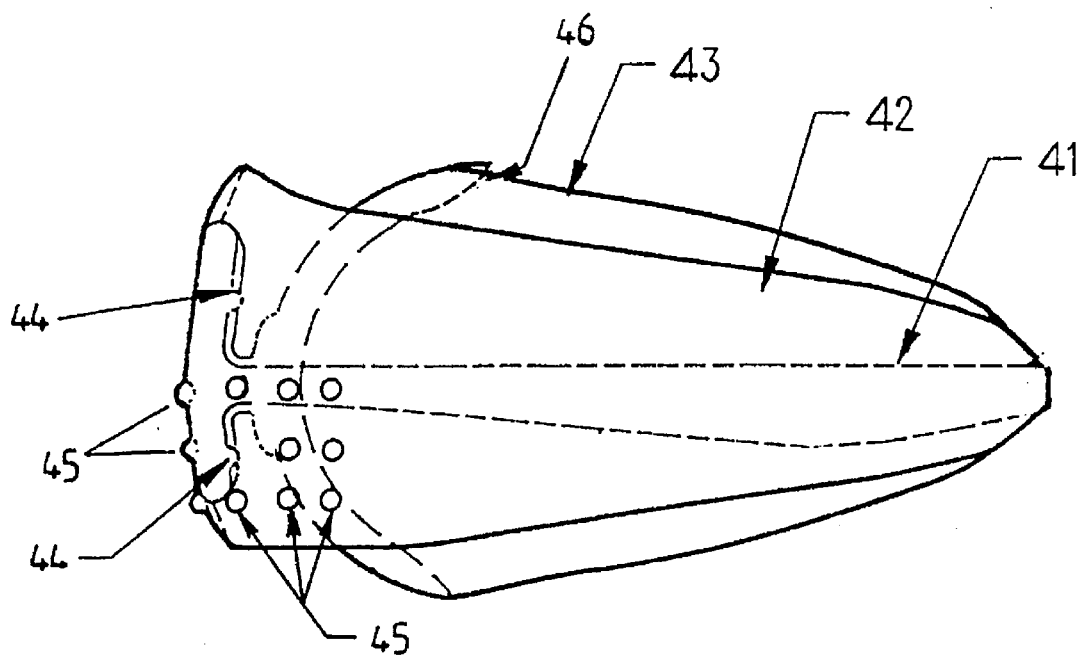
FIG. 18 is a side elevational view of a second form of appliance according to the invention.
Figure 19:
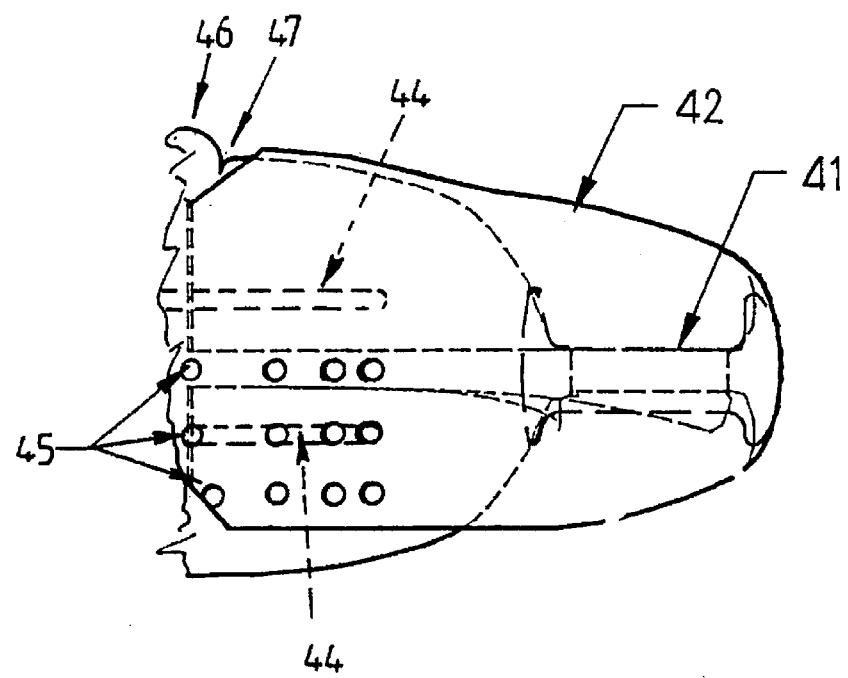
FIG. 19 is a half front elevational sectional view of the appliance of FIG. 18.
Figure 20:
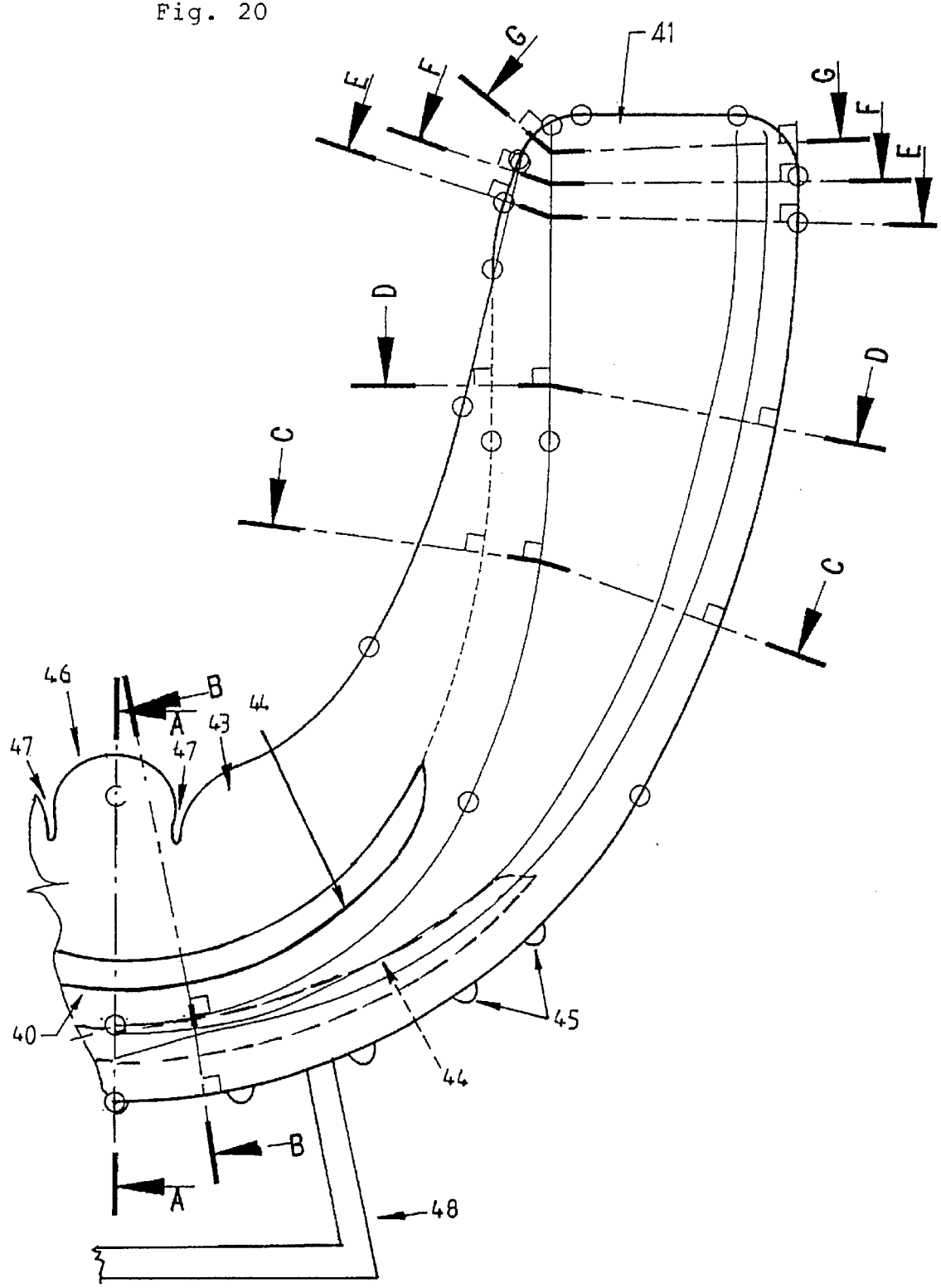
FIG. 20 is an enlarged half-plan view of the appliance of FIG. 18.

Referring now to FIG. 17 there is illustrated a further embodiment of appliance 35 according to the invention suitably for use as a dummy or pacifier for babies or young children. Again like parts to the previous embodiments have been given like numerals. In this form, the appliance 35 is provided with an integral handle portion 36 which projects outwardly from the central portion of the appliance 35 to be normally located outside the mouth. Preferably, the handle portion 36 includes an enlarged head 37 of any suitable form to facilitate gripping. The handle portion 37 may be formed of hard plastics material and either as stated above be formed integrally with the main body of the appliance 35 or secured thereto in any suitable fashion. It will be apparent in this form that the appliance 35 is considerably smaller in dimensions than the appliance described with reference to FIGS. 1 to 15 so as to suit the size of baby's mouths. As with the other type of appliances, however, this appliance may be made different sizes so as to suit a range of mouth sizes.

Referring now to FIGS. 18 to 22, there is illustrated an alternative form of appliance 40 according to the present invention particularly adapted for orthodontic and orthopaedic correction in the facial area of children. The appliance 40 has many features in common with the appliance 10 of FIGS. 1 to 15 including a base portion 41 of generally aerofoil shape in cross section and inner and outer flange portions 43 and 42 respectively. The base portion 41 is generally parabolic in plan view to be approximately the shape of the average child's arches. Preferably, the appliance is made in two sizes to accommodate the ages 2 to 5 years and 6 to 11 years with the base portion 41 preferably having a length of 30 mm and 40 mm respectively, the longer length being to accommodate newly erupted molars. The thickest part of the base portion 41 is preferably 2 to 3 mm thicker than the thickness of the anterior-posterior parts of the base portion 41.

The outer flange portion 42 includes on its inner surface on the upper and lower sides of the base portion 41 respective ribs 44 which are spaced from the base portion 41 and extend inwardly towards the opposite flange portion 43 and generally parallel to the base portion 41. These ribs 44 are positioned to lie on the labial surfaces of the upper and lower anterior teeth to improve their alignment.

The outer flange portion 42 also includes on its outer surface and on its lower half, a plurality of outwardly directed projections 45 which serve as bumpers to discourage contraction of the mentalis muscle which lies in use proximal to this surface. This muscle is implicated in malocclusion of the lower front teeth. The thickness and material flexibility of the outer flange portion give it the compromise between adaptability to many mouth and tooth sizes and also sufficient tension to align the teeth.

The inner flange portion 43 as before is of complex shape in plan and side view being generally parabolic in cross section with deepening curves towards its distal ends. The middle section of the upper section of the inner flange portion is formed as before to have a tab 46 which is thicker that the adjacent sections of the flange portion 43 and projects towards the tongue in use to provide stimulus to the tongue to position it in a particular manner. As before, the cut-away sections 47 on either side of the tab 46 not only define the shape of the tab 46 but also permit the appliance 40 to adapt to wide ranging arch and tooth sizes without distortion of the central section and thus the entire appliance.

The above arrangement is only provided on the upper portion of the appliance 40. At the lower side, the surface of the inner flange has a double convex curvature to sit against the teeth and provide a forward force on the teeth to position them further forward. This force also acts antagonistically to the projecting ribs 44 on the inner surface of the outer flange 42. This allows the appliance to straighten teeth without fixed or removable appliances of special construction.

For preschool usage the appliance 40 may include a handle portion 48 (see FIG. 20) to enable easy placement of the appliance within the mouth cavity and removal therefrom.

Figure 21:
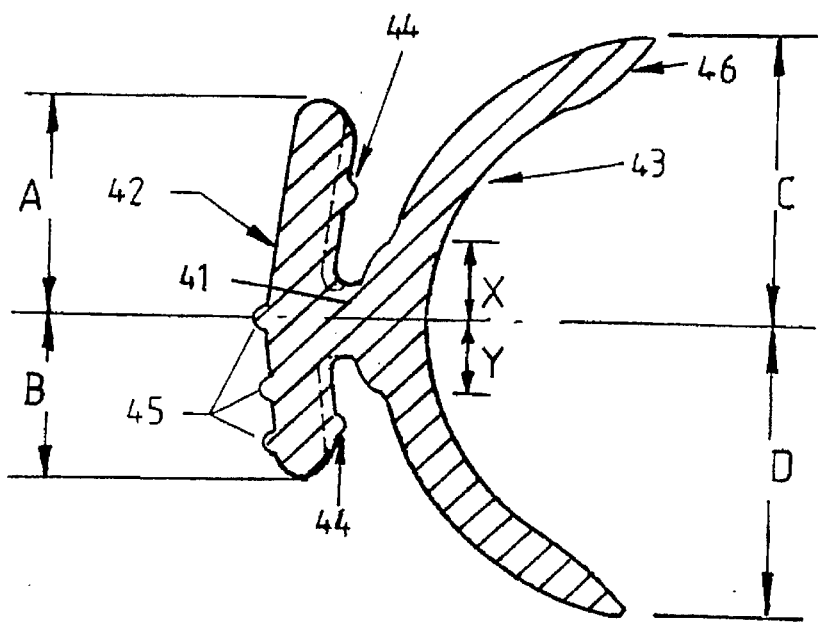
FIGS. 21 and 22 are sectional views along line A—A and line B—B of FIG. 20 respectively.
Figure 22:
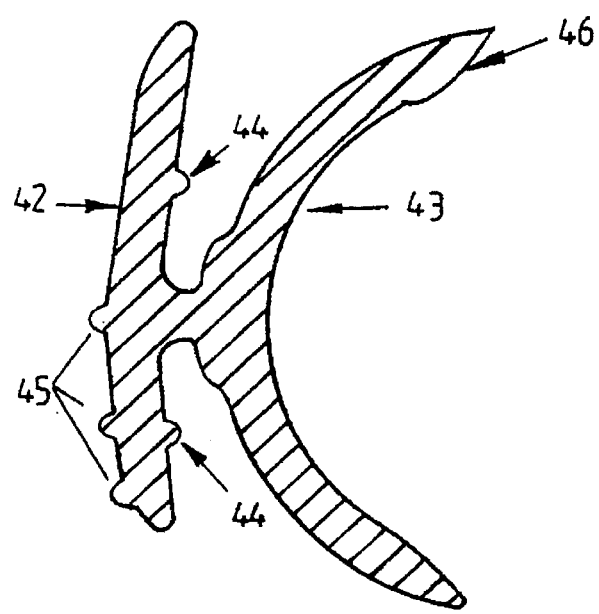

Typically and with reference to FIG. 21 the dimensions A, B, C and D for a preschool appliance are at the centre of the appliance 8 mm, 6 mm, 8 mm and 8 mm respectively. For primary school usage those dimensions are typically 12 mm, 9 mm, 10 mm and 10 mm respectively. For a preschool appliance the dimensions X and Y in FIG. 21 are typically 2 mm and 1.5 mm or 3 mm and 2.5 mm for primary school children. Suitable the ribs 44 have a thickness of approximately 1.5 mm and their typical spacing from the surface of the base portion 41 of the appliance is between 3 mm and 4.5 mm on the upper side and between 2 mm and 4 mm on the lower side.

In a further simplified form of the apparatus a single slot or cut-out portion may be provided on the inner flange at the midline, the cut-out portion for example being of V-shaped form so as to allow for lateral adjustment of the appliance.

Figure 14:
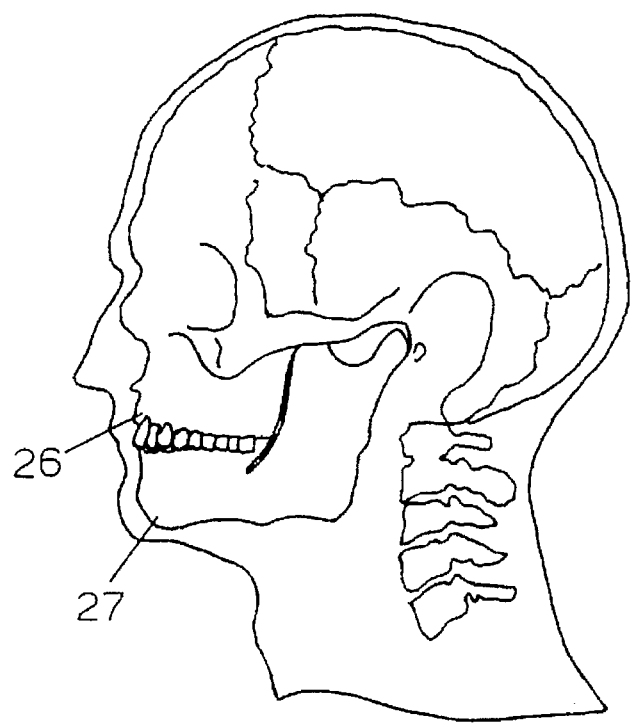
FIG. 14 illustrates schematically a skull and jaw in an unbalanced state.
Figure 15:
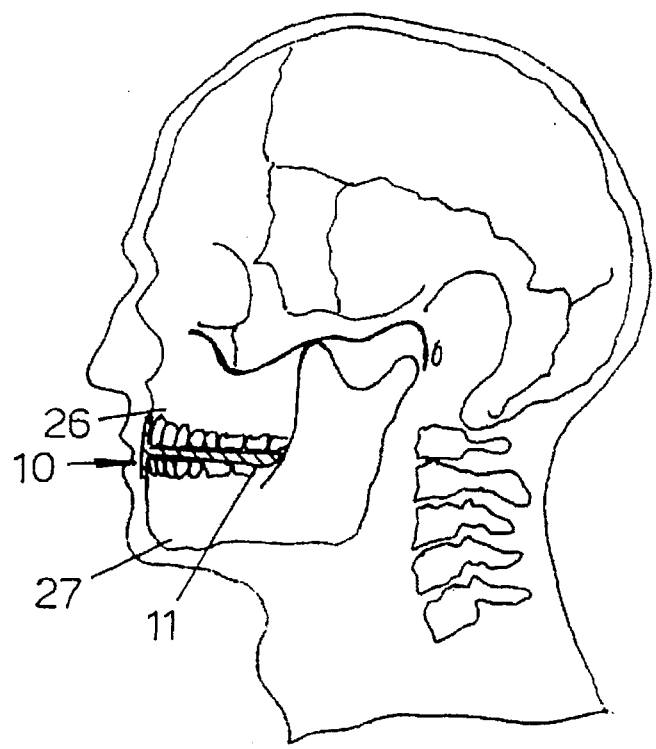
FIG. 15 illustrates the manner in which the oral appliance of FIG. 1 repositions the jaws.

In use, the appliance 10 is applied to the mouth of the user and the effect of the inner and outer flange portions 12 and 13 is to promote relaxation of the muscles controlling the lower jaw so as to also relax the reciprocal muscles of the head and neck. This is further facilitated by the shape of the base portion 11 which supports the lower jaw and encourages the lower jaw assume its anatomically correct relationship with the upper jaw. Relaxation of the aforesaid muscles in the head and neck will decrease the majority of muscle tension headaches. This will be further apparent from FIGS. 14 and 15 where as shown in FIG. 14, the misaligned upper jaw 31 and lower jaw 32 come together incorrectly with the lower jaw 32 and teeth disposed rearwardly of the upper jaw 31 and teeth in a non-perfect bite situation, this causing muscle overload and also the cervical vertebrae to be incorrectly aligned thus leading to pain in the user.

Where the appliance 10 of the present invention is employed as shown in sectional view in FIG. 15 and when the teeth are closed on the appliance 10 the jaws 31 and 32 are repositioned, the lower jaw 32 moving downwardly and outwardly to the perfect bite position with the teeth in substantial alignment with the teeth of the top jaw 31 so that stretching of the muscles does not occur which accordingly reduces the symptoms of muscle tension headaches.

When used for headache relief or relief of neck pain, the appliance 10 is placed into the mouth and the teeth closed upon the appliance lightly to move the jaws into a more balanced position. It is preferred that a person suffering from headaches sit quietly in a relaxed position for a minimum of one hour, whilst assuring the neck and head are well supported. The appliance may be used as required when headaches are most severe.

For exercising the head and neck muscles and to improve oxygen flow to the face muscles, the appliance 10 may be used actively being gently chewed for 10 minutes. The appliance 10 can also be worn at night whilst sleeping to alleviate teethgrinding, morning stiffness or morning headaches.

Regular use of the appliance of the invention will serve to reprogram the Cranio-Mandibular area and retrain the muscles into functioning as intended. Additionally, the appliance trains the tongue and muscles associated therewith to function correctly in the manner described above. The shape of the appliance and relative dimensions make the appliance almost universally adaptable to adult mouths without moulding or adjusting. The appliance additional encourages nose breathing by obliterating the oral airways.

Preferably, the appliance is formed of silicon rubber or medical PVC material, however, any other flexible synthetic or natural material may be suitable for forming the appliance.

This appliance of FIG. 16 which can be mass produced in several sizes is designed to increase the available strength in athletes by holding the jaws in their optimum strength position. The appliance which suitably is formed of a medicinal PVC may be used in all sports but specifically for golf, tennis, weightlifting and athletics.

The appliance of FIG. 17 is used in a conventional manner as a dummy or pacifier and the inner and outer flange portions 12 and 13 help pacify children and the shape of the flanges promote correct tongue position and dental eruption. Furthermore, when chewed, the appliance does not have the adverse orthodontic effects of conventional dummies.

The appliance of FIGS. 18 to 22 when placed in the mouth and progressively chewed upon by the growing child and then held passively will encourage the tooth jaw alignment and functional adaption necessary to normalize a developing malocclusion provided that the appliance is used regularly and daily for a minimum of 6 months.

I claim:

1. An oral appliance adapted for repositioning the temporomandibular joint, said appliance including a base portion having a generally U-shaped plan form and including opposite integrally formed side arms adapted for location between the teeth of the upper and lower jaws of a user, said side arms having leading and trailing edges, and outer and inner flange portions integrally formed with said side arms and extending along the leading and trailing edges thereof so as to form upper and lower channels for accepting the teeth of the upper and lower jaws, each said side arm having a leading end and a trailing end and tapering in thickness along said channels on each side of said appliance from regions forwardly of but adjacent to the trailing ends of said arms towards the leading end thereof whereby the side arms may be adapted to substantially occupy space between said teeth of said upper and lower jaws so as to provide a support for the jaws of the user, and said inner flange portion on the upper side of said arms being provided with a slot or cutaway region arranged at or adjacent the midline of said appliance to permit said arms to move towards and away from each other and thus allow said appliance to adjust laterally to fit the jaws of the user.

2. An appliance according to claim 1 wherein said arms taper in thickness from said regions to the trailing ends of said arms so as to substantially occupy the space between the upper and lower jaws.

3. An appliance according to claim 2 wherein said tapering thickness in said arms is achieved by forming said arms on opposite sides of the appliance asymmetrically with the top side of said arms being generally planar or flat.

4. An appliance according to claim 3 wherein said arms in longitudinal cross section are formed as an asymmetric aerofoil shape with the asymmetric or curved surface thereof being disposed on the lower side of said appliance and the maximum depth of the aerofoil being located at a said region on opposite sides of said appliance.

5. An appliance according to claim 1 wherein said inner flange portions define in cross section a concave recess for receiving the tongue of the user.

6. An appliance according to claim 1 wherein said inner flange portion includes on the upper side of said arms a trailing edge, said slot or cut away region extending inwardly from said trailing edge.

7. An oral appliance according to claim 1 wherein said outer flange portion includes on its inner side, proximate the leading end of said base portion, upper and lower transversely extending rib means on opposite sides of said base portion respectively.

8. An oral appliance adapted for repositioning the temporomandibular joint, said appliance including a base portion, said base portion being of generally U-shaped or parabolic plan form and including opposite integrally formed side arms adapted for location between the teeth of the upper and lower jaws of a user, said side arms having leading and trailing edges, outer and inner flange portions integrally formed with said side arms and extending along the leading and trailing edges thereof and to opposite sides thereof so as to form upper and lower channels for accepting the teeth of the upper and lower jaws, said side arms having a cross sectional form adapted to substantially occupy space between said teeth of said upper and lower jaws so as to provide a support for the jaws of the user, and said inner flange portion on the upper side of said arms being provided with a slot or cutaway region arranged at or adjacent the midline of said appliance to permit said arms to move towards and away from each other and thus allow said appliance to adjust laterally to fit the jaws of the user, and wherein said inner flange portion on the upper side of said arms is provided with a pair of spaced said slots or cutaway regions disposed symmetrically on opposite sides of the midline of the appliance to define therebetween a tab.

9. An appliance according to claim 8 wherein said tab has an increased thickness relative to the remainder of said inner flange portion to provide an abutment for the tongue of the user whereby the tongue is encouraged or reminded to adopt a normal position.

10. An appliance according to claim 9 wherein said inner flange portions on opposite sides of said arms are thickened or enlarged adjacent said arms to adapt said appliance to the shape of the teeth of the user.

11. An oral appliance for orthodontic or orthopedic correction, said appliance including a base portion shaped so as to be locatable between the teeth of the upper and lower jaws of a user, and outer and inner flange portions along the leading and trailing edges of said base portion and extending to opposite sides thereof so as to form upper and lower channels for accepting the teeth of the upper and lower jaws and wherein said base portion has a cross sectional form adapted to substantially occupy space between said teeth of said upper and lower jaws so as to provide a support for the jaws of the user, said outer flange portion being provided with rib means on its inner surface on opposite sides of and spaced from said base portion, said rib means extending generally parallel to said base portion and adapted to in use engage the teeth of the user, said inner flange portion on the upper side of said base portion including a cut-away region or slot to allow for lateral adjustment of the appliance.

12. An appliance according to claim 11 wherein an integral enlargement is formed at the junction of the inner flange portion and base portion on both sides thereof so that the teeth of the user are positioned in use between said enlargements and said rib means on the inner surface of the outer flange portion.

13. An appliance according to claim 11 or claim 12 wherein said outer flange portion is provided on its outer side with a series of protrusions for engaging the mentalis muscle in use.

14. An appliance according to claim 11 wherein said inner flange portions define in cross section a concave recess for receiving the tongue of the user.

15. An appliance according to claim 11 wherein said inner flange portion includes on the upper side of said arms a trailing edge, said slot or cut-away region extending inwardly from said trailing edge.

16. An oral appliance adapted for repositioning the temporomandibular joint, said appliance including a base portion, said base portion being of generally U-shaped plan form and including opposite side arms adapted for location between the teeth of the upper and lower jaws of a user, said side arms having leading and trailing edges, and outer and inner flange portions extending along the leading and trailing edges thereof and to opposite sides thereof so as to form upper and lower channels for accepting the teeth of the upper and lower jaws, said side arms having in longitudinal cross sectional, a form adapted to substantially occupy space between said teeth of said upper and lower jaws so as to provide a support for the jaws of the user, and said inner flange portion on the upper side of said arms being provided with a rearwardly extending tab arranged at the midline of said appliance, said tab providing an abutment for the tongue of the user whereby the tongue is encouraged or reminded to adopt a normal position.

17. An oral appliance according to claim 16 wherein said tab is defined between a pair of spaced apart slots, said slots permitting lateral adjustment of said appliance to fit the jaws of a user.

18. An oral appliance according to claim 16 wherein said tab is thickened relative to the remainder of said inner flange portion.

19. An oral appliance formed of a flexible plastics material and having a U-shaped base portion and integrally formed inner and outer flanges which define with said base portion upper and lower U-shaped channels for receiving the teeth of the upper and lower jaws of a user, said inner flange having on its upper side a trailing edge and at least one slot extending inwardly from said trailing edge and arranged at or adjacent to the midline of said appliance, said slot permitting lateral adjustment said appliance whereby to permit variation of the width of said appliance to fit the jaws of a user.

20. An oral appliance according to claim 19 wherein said inner flange includes on its upper side, at least a pair of spaced said slots on opposite sides of said midline and defining therebetween a rearwardly extending tab forming an abutment for the tongue of the user.

\* \* \* \* \*